(12) United States Patent
O'Leary et al.

(10) Patent No.: US 11,691,036 B2
(45) Date of Patent: Jul. 4, 2023

(54) MACROCYCLIC KETONE AS MALODOR COUNTERACTING INGREDIENT

(71) Applicant: FIRMENICH SA, Satigny (CH)

(72) Inventors: Nicholas O'Leary, Plainsboro, NJ (US); Jonathan Williams, Southall (GB); Monica Bandera, Geneva (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 17/659,791

(22) Filed: Apr. 19, 2022

(65) Prior Publication Data

US 2022/0249877 A1    Aug. 11, 2022

Related U.S. Application Data

(63) Continuation of application No. 16/244,052, filed on Jan. 9, 2019, now abandoned, which is a continuation of application No. 15/535,623, filed as application No. PCT/EP2015/079185 on Dec. 10, 2015, now abandoned.

(30) Foreign Application Priority Data

Dec. 18, 2014 (EP) .................................... 14198796

(51) Int. Cl.
*A61Q 13/00* (2006.01)
*A61K 8/35* (2006.01)
*A61Q 15/00* (2006.01)
*C11D 3/00* (2006.01)
*C11D 3/50* (2006.01)
*C07C 49/607* (2006.01)
*C11B 9/00* (2006.01)

(52) U.S. Cl.
CPC ................ *A61Q 13/00* (2013.01); *A61K 8/35* (2013.01); *A61Q 15/00* (2013.01); *C07C 49/607* (2013.01); *C11B 9/0038* (2013.01); *C11D 3/0068* (2013.01); *C11D 3/50* (2013.01); *C11D 3/505* (2013.01)

(58) Field of Classification Search
CPC ...................................................... A61Q 13/00
See application file for complete search history.

(56) References Cited

U.S. PATENT DOCUMENTS

| 5,538,719 A | 7/1996 | Preti et al. |
| 2014/0135402 A1 | 5/2014 | Fankhauser |

FOREIGN PATENT DOCUMENTS

WO    2012175437 A1    12/2012

OTHER PUBLICATIONS

International Search Report and Written Opinion for corresponding PCT/EP2015/079185 dated Feb. 5, 2016; 8 pages.

*Primary Examiner* — Arrie L Reuther
(74) *Attorney, Agent, or Firm* — Armstrong Teasdale LLP

(57) ABSTRACT

The present invention relates to the field of perfumery. More particularly, it concerns malodor masking compositions and/or ingredients, as well as method for counteracting or masking malodors and perfuming compositions having odor masking properties.

7 Claims, No Drawings

MACROCYCLIC KETONE AS MALODOR COUNTERACTING INGREDIENT

CROSS-REFERENCE TO RELATED APPLICATIONS

This application is a Continuation Application of U.S. patent application Ser. No. 16/244,052, filed Jan. 9, 2019, which is a Continuation Application of U.S. patent application Ser. No. 15/535,623, filed Jun. 13, 2017, which is a Continuation Application of International Patent Application No. PCT/EP2015/079185, filed Dec. 10, 2015, which claims priority to EP Application No. 14198796.6, filed Dec. 18, 2014, the contents of which are incorporated herein by reference in their entirety.

TECHNICAL FIELD

The present invention relates to the field of perfumery. More particularly, it concerns malodor masking compositions and/or ingredients, as well as a method for counteracting or masking malodors and perfuming compositions having odor masking properties.

PRIOR ART

Malodorous smells exist in many environments and are experienced in our day life. Such odors are created in any environment. In particular one may cite the commercial and residential environment malodors which can be generated by, for example, waste products, trash receptacles, toilets, cat litter, and food handling and processing. Bathroom (including feces or urine), kitchen and body malodors are just a few of the common environmental sources of malodors in daily life. Said malodors are complex mixtures of more than one malodorant compound which may typically include various amines, thiols, sulfides, short chain aliphatic and olefinic acids, e.g. fatty acids, derivatives.

Residential or body related malodors typically include indole, skatole, and methanethiol found in feces malodor; piperidine and morpholine found in urine; pyridine and triethyl amine found in kitchen and garbage malodors; and short chain fatty acids, such as 3-methyl-3-hydroxyhexanoic acid, 3-methylhexanoic acid or 3-20 methyl-2-hexenoic acid, found in axilla malodors.

Obviously such malodors are not pleasant for humans are therefore there is a constant need for malodor counteracting (MOC) solutions decreasing or suppressing the perception of malodors. Various approaches exist to achieve such goal with MOC compositions, and include i) masking which relates to suppression or decrease of the perception of a malodor by various mechanism such as a receptor antagonist activity. (It is useful to note that "masking" is per se different from a standard perfumery use consisting in covering or superimposing a pleasant stronger odor over the malodor) and/or ii) suppression which consists in either suppressing or decreasing the perception by just chemically or physically eliminating the malodor or its generation (e.g. by having an antimicrobial activity).

However the task is generally very difficult because the chemicals responsible for the malodor are extremely powerful and detectable already at level much lower than the one of the chemical compounds used for classical MOC activity, so that one have to use over excessive amount of MOC composition/compounds to achieve an acceptable malodor counteracting action.

The present invention compounds have been reported in the literature for a use as perfuming compounds (WO 2012/175437). However, such prior art document do not anticipate the use of the present compound also as MOC ingredient.

The aim of the present invention is to provide a malodor counteracting or MOC composition capable of being highly effective in particular against the body, residential and/or pet malodors.

DESCRIPTION OF THE INVENTION

We have now surprisingly discovered that a compound of formula

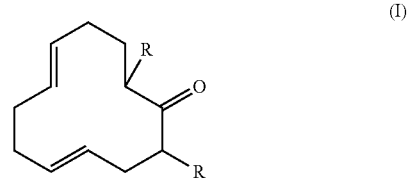

(I)

wherein one R group is a hydrogen atom and the other is a hydrogen atom or a $C_{1-3}$ alkyl group; and
each carbon-carbon double bond of said compound, independently from each other, can be in a configuration Z or E or a mixture thereof;
can be used as malodor counteracting, in particular for counteracting body, residential and pet malodor type.

For the sake of clarity, by the expression "a compound of formula (I) wherein [ . . . ] and each carbon-carbon double bond of said compound, independently from each other, can be in a configuration Z or E or a mixture thereof" it is meant also a composition of matter comprising the various (E,E), (E,Z) or (Z,E) and (Z,Z) isomers of 4,8-cyclododecadien-1-one, 12-methylcyclododeca-4,8-dienone and/or 2-methyl-cyclododeca-4,8-dienone.

According to any one of the above embodiments of the invention, one R group is a hydrogen atom and the other is a hydrogen atom or a methyl or ethyl group. In particular both R represent a hydrogen atom.

For the sake of clarity, by the expression "each carbon-carbon double bond of said compound, independently from each other, can be in a configuration Z or E or a mixture thereof" it is meant the normal meaning in the art, i.e. that said compound (I) can be in the form of an essentially pure stereoisomer (i.e. the (4E,8E) one) or in the form of a mixture of stereoisomers, e.g in a mixture comprising the stereoisomers (4E,8E), (4Z,8E) and (4E,8Z) in various w/w ratio.

In particular, the invention's compound can be in the form of a mixture containing predominantly the stereoisomers (4E,8E), (4Z,8E) and (4E,8Z), the remaining being essentially the (4Z,8Z) stereoisomer. In such a case, one may define a w/w ratio (4E,8E)/[(4Z,8E)+(4E,8Z)] for such mixture of stereoisomers (also referred to as the (E,E)/((E,Z) ratio). According to a particular aspect of said embodiment, the compound (I) is in the form of a mixture of stereoisomers having a (E,E)/((E,Z) ratio comprised between 20/80 and 1/99. According to said embodiment, said mixture of stereoisomers has a (E,E)/((E,Z) ratio comprised between 15/85 and 2/98.

Alternatively said compound (I) is in the form of a mixture of stereoisomers having a (E,E)/((E,Z) ratio comprised between 80/20 and 99.5/0.5. According to said embodiment, said mixture of stereoisomers has a (E,E)/((E,Z) ratio comprised between 90/10 and 99/1.

For the sake of clarity, by the expression "predominantly" it is meant that the mentioned stereoisomer or mixture of stereoisomers represents more than 90% of said compound (I), the remaining being obviously in the form of the other isomers.

As specific examples of the invention's compounds, one may cite, as non-limiting example, 4,8-cyclododecadien-1-one in the form of a mixture comprising about 99% w/w of (4E,8E)-4,8-cyclododecadien-1-one and about 1% w/w of the (4Z,8E)-4,8-cyclododecadien-1-one and (4E,8Z)-4,8-cyclododecadien-1-one stereoisomer (i.e. a 4,8-cyclododecadien-1-one in the form of a (E,E)/(E,Z) mixture 99/1 w/w, and also herein after referred to as "Compound 1").

As other example, one may cite 4,8-cyclododecadien-1-one in the form of a mixture comprising at least 90% w/w of (4E,8Z)-4,8-cyclododecadien-1-one and (4Z,8E)-4,8-cyclododecadien-1-one stereoisomers and about 5% w/w of the (4E,8E)-4,8-cyclododecadien-1-one stereoisomer (i.e. a 4,8-cyclododecadien-1-one in the form of a (E,E)/(E,Z) mixture of below 5/90 w/w, and also herein after referred to as "Compound 2").

As other specific, but non-limiting, examples of the invention's compounds, one may cite the following ones in Table 1:

TABLE 1

Invention's compounds

Compound structure and name

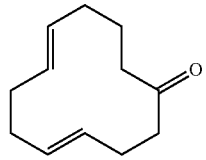 [SMILES: O=C1CC/C=C/CC/C=C/CCC1]

4,8-cyclododecadien-1-one in the form of a (E,E)/(E,Z) mixture

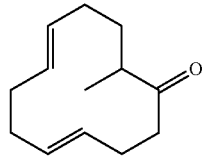

(4E,8E)-12-methylcyclododeca-4,8-dienone

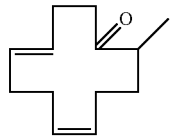

(4E,8Z)-12-methylcyclododeca-4,8-dienone

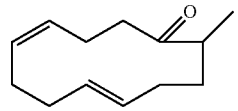

(4Z,8E)-12-methylcyclododeca-4,8-dienone

TABLE 1-continued

Invention's compounds

Compound structure and name

Mixture containing the various (Z,E) and (E,E) of isomers 12-methylcyclododeca-4,8-dienone and 2-methylcyclododeca-4,8-dienone According to a particular embodiment of the invention, the compounds of formula (I) are selected from the group consisting of (4E,8E)-4,8-cyclododecadien-1-one, (4Z,8E)-4,8-cyclododecadien-1-one, (4E,8Z)-4,8-cyclododecadien-1-one, (4E,8E)-12-methylcyclododeca-4,8-dienone, (4E,8Z)-12-methylcyclododeca-4,8-dienone, (4Z,8E)-12-methylcyclododeca-4,8-dienone, 2-methylcyclododeca-4,8-dienone and the mixtures thereof.

As mentioned above, the invention concerns the use of the above defined compound as a MOC ingredient, e.g. to modify, suppress, reduce, decrease or mask the sensory perception of a body, residential and/or pet malodor. In other words, it concerns a method to modify, suppress, reduce, decrease or mask a malodor such as body, residential and/or pet malodor, which method comprises the step of releasing into the air, or over a surface or the malodor source, an effective amount of at least one invention's compound. By "use of at least one invention's compound" it has to be understood here also the use of any MOC composition containing a compound of formula (I).

According to any embodiment of the invention, the malodor counteracted by a compound of formula (I) is more specifically of the kitchen, bathroom, tobacco, pet, and/or body type.

As non-limiting examples of kitchen malodor one may cite any type of malodor present in a residential or commercial kitchen including, but not limited to: kitchen garbage odors that may result from the disposal of raw or cooked meat, fish, vegetables, fruit and/or dairy products; odors experienced during food preparation, especially odors generated from raw fish, raw garlic and raw onions; cooking odors, especially odors produced when cooking meat, fish, onion and/or garlic; the odor of cooking oil used for frying foods; burnt odors that may originate from the over-cooking or burning of foods; odors originating from the kitchen sink drain; odors originating from in-sink disposal units; and, odors originating from a refrigerator.

As non-limiting examples of bathroom malodor one may cite any malodor type of malodor present in a residential or public bathroom/restroom including, but not limited to: odors present immediately after the use of the toilet; lingering toilet odors; stale urine odor; and, moldy or musty odors that often originate in damp areas of the bathroom such as around the bath or shower.

As non-limiting examples of tobacco odor one may cite the odor generated during smoking of cigarettes, cigars or tobacco pipes or it may be the stale smoke odor that lingers after use of tobacco products in a room or it may be the odor originating from an ash tray that comprises debris from cigarettes, cigars or tobacco pipes.

As non-limiting examples of pet odor one may cite any type of odor associated with a domestic pet, especially a cat or a dog, and includes, but is not limited to: fecal odors from litter boxes; urine odors from litter boxes; lingering urine odors; wet-dog odor; and, pet-bed odor.

As non-limiting examples of body malodor one may cite any type of odor produced by the human body including, but not limited to: axillary (armpit) odor, scalp odor, foot odor and vaginal odor. It has to be understood here that "body malodor" may also mean an odor that originates on the human body and is transferred to another substrate such as a textile; this may include, for example, the odor of worn socks, or the odor of worn sportswear.

According to any embodiment of the invention, said malodor is more specifically of the kitchen, bathroom and/or body type.

According to any embodiment of the invention, the invention's compound is used, as above described, against said malodor which is generated by the presence of skatole, $C_{1-7}$ aliphatic carboxylic acids, methyl morpholines, thioglycolic acid, $C_{1-4}$ dialkyl sulfide or disulfide or trisulfide, indol, urea and/or $C_{1-7}$ thiols or mixtures thereof.

According to any embodiment of the invention, the masking above mentioned can be obtained through the application of any known consumer product relevant for the targeted surface.

According to any embodiment of the invention, said surface is the skin, a bathroom, a toilet, a kitchen surface (e.g. a trash) or a fabric (like clothing, bed sheets, carpet, a sofa or a curtain).

Accordingly, the present invention refers in a further embodiment to the non-therapeutic use of an invention's compound for the reduction of the sensory perception of malodor by a human.

Without being bound by theory, it is believed, that the invention's compound, as hereinabove defined, do act through a mechanism related to odor suppression (e.g. through antimicrobial activity) and/or masking.

Said invention's compound, which in fact can be advantageously employed as MOC compound, is also an object of the present invention.

It is understood by a person skilled in the art that the invention's compound, as defined herein, may be added into an invention's composition in neat form, or in a solvent, or they may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof, or they may be chemically bound to substrates which are adapted to release the compounds upon application of an exogenous stimulus such as light, enzymes, or the like. Therefore when referring to the invention's compound it is also intended any of its form above mentioned.

Therefore, another object of the present invention is a MOC composition comprising:
i) as a MOC ingredient, at least one invention's compound as defined above;
ii) at least one ingredient selected from the group consisting of a perfumery carrier and a perfumery base;
iii) at least one other MOC compounds; and
iv) optionally at least one perfumery adjuvant.

It is understood that said MOC composition, by its nature in also a perfuming one.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

By "other MOC compounds" we mean here a material which is already known for a MOC activity and is commonly used in the industry for such use. Said other MOC compound can be included to further boost, or complement, the MOC activity of the invention's MOC composition.

Said other MOC compounds include, but are not limited to, antimicrobial agents, malodor absorbers, chemical neutralisers e.g. acid-base reagents, thiol traps, odour blockers, cross-adaptation agents e.g. as disclosed in U.S. Pat. No. 5,538,719 incorporated herein by reference, malodor complexation agents e.g. various cyclodextrins.

Examples of antimicrobial agents include, but are not limited to, metal salts such as zinc citrate, zinc oxide, zinc pyrethiones, and octopirox; organic acids, such as sorbic acid, benzoic acid, and their salts; parabens, such as methyl paraben, propyl paraben, butyl paraben, ethyl paraben, isopropyl paraben, isobutyl paraben, benzyl paraben, and their salts; alcohols, such as benzyl alcohol, phenyl ethyl alcohol; boric acid; 2,4,4'-trichloro-2-hydroxy-diphenyl ether; phenolic compounds, such as phenol, 2-methyl phenol, 4-ethyl phenol; essential oils such as rosemary, thyme, lavender, eugenol, geranium, tea tree, clove, lemon grass, peppermint, or their active components such as anethole, thymol, eucalyptol, farnesol, menthol, limonene, methyl salicylate, salicylic acid, terpineol, nerolidol, geraniol, and mixtures thereof.

Examples of malodor absorbers include, but are not limited to molecular sieves, such as zeolites, silicas, aluminosilcates, and cyclodextrins; and organic absorbents, such as for example, activated charcoal, dried citrus pulp, cherry pit extract, corncob, and mixtures thereof.

An invention's composition consisting of at least one an invention's compound and at least one perfumery carrier and at least another MOC ingredient represents a particular embodiment of the invention.

It is useful to mention here that the possibility to have, in the compositions mentioned above, more than one compound of formula (I) is important as it enables the person skilled in the art to prepare MOC compositions possessing an activity fine-tuned toward the targeted malodor or source of malodor, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a MOC composition according to the invention as far as said mixture does not provide the inventive compound in a suitable form. Thus, unpurified reaction mixtures are generally excluded from the present invention unless otherwise specified.

Furthermore, the invention's compound can also be advantageously used in any consumer product for which it may be useful to have a MOC activity at least. Consequently, another object of the present invention is represented by a MOC consumer product comprising, as an active ingredient, at least one invention's composition, as defined above.

The invention's compound or composition can be added as such or as part of an invention's a MOC composition.

It is understood that said MOC consumer product, by its nature can also be a perfuming one.

For the sake of clarity, it has to be mentioned that, by "MOC, and optionally perfuming, consumer product" or the similar, it is meant a consumer product which is expected to deliver at least a MOC effect, and optionally also a pleasant perfuming effect, to the surface to which it is applied (e.g. skin, hair, textile, or home surface, but also air). In other words, a consumer product according to the invention is a perfumed consumer product which comprises the functional formulation, as well as optionally additional benefit agents, corresponding to the desired consumer product, e.g. a detergent or an air freshener, and an effective amount of at least one invention's compound. For the sake of clarity, said consumer product is a non-edible product.

The nature and type of the constituents of the MOC consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be:
- a perfume, such as a fine perfume, an Eau de Toilette, a cologne or an after-shave lotion;
- a fabric care product, such as a liquid detergent, a powder detergent, detergent tablets, a detergent bar, a detergent paste, a liquid fabric softener, fabric softener sheets, a fabric scent booster, a laundry pre-treatment, a fabric refresher, an ironing water, a laundry bleach, a carpet powder or a carpet cleaner;
- a hair care product, such as a shampoo, a hair conditioner, a hair cream, a hair oil, a hair styling product (such as a spray, mousse or gel), a hair coloration product or a hair permanent wave product;
- a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;
- a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;
- a skin-cleansing product, such as a soap bar, a shower gel, a liquid hand soap, a bath foam or an intimate wash product;
- an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or
- a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

Some of the above-mentioned MOC consumer product may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the invention as set forth in the appended claims.

The proportions in which the compound according to the invention can be incorporated into the various aforementioned products or compositions vary within a wide range of values. These values are dependent on the nature of MOC consume product and on the desired organoleptic effect as well as the nature of the co-ingredients in a given composition when the compound according to the invention are mixed with other ingredients, solvents or additives commonly used in the art.

In general, for example, in the case of perfuming compositions, typical concentrations are in the order of 0.001% to 5% by weight, or even more, of the compound of the invention based on the weight of the composition into which they are incorporated. Concentrations lower than these, such as in the order of 0.01% to 100% by weight, can be used when the invention's composition are incorporated into MOC consumer products, percentage being relative to the weight of the consumer product.

In particular, the concentration of MOC composition according to the invention used in the various aforementioned consumer products varies within a various wide range of values depending on the nature of the consumer product. For instance, a MOC composition according to the invention can be used in a perfume product at a concentration of 0.01% to 50% by weight, preferably at a concentration of 0.2% to 40% by weight, most preferably at a concentration of 0.5% to 25% by weight. For instance, a MOC composition according to the invention can be used in a fabric care product at a concentration of 0.01% to 20% by weight, preferably at a concentration of 0.05% to 10% by weight, most preferably at a concentration of 0.1% to 5% by weight. Yet for instance, a MOC composition according to the invention can be used in a hair care product at a concentration of 0.01% to 10% by weight, preferably at a concentration of 0.05% to 5% by weight, most preferably at a concentration of 0.1% to 3% by weight. For instance, a MOC composition according to the invention can be used in a skin care product at a concentration of 0.01% to 10% by weight, preferably at a concentration of 0.05% to 5% by weight, most preferably at a concentration of 0.1% to 2.5% by weight. For instance, a MOC composition according to the invention can be used in a body deodorant or antiperspirant product at a concentration of 0.01% to 10% by weight, preferably at a concentration of 0.05% to 7% by weight, most preferably at a concentration of 0.1% to 5% by weight. Yet for instance, a MOC composition according to the invention can be used in a skin cleansing product at a concentration of 0.01% to 5% by weight, preferably at a concentration of 0.05% to 3% by weight, most preferably at a concentration of 0.1% to 2.5% by weight. For instance, a MOC composition according to the invention can be used in an air freshening product at a concentration of 0.01% to 100% by weight. For instance, a MOC composition according to the invention can be used in a surface care product at a concentration of 0.001% to 10% by weight, preferably at a concentration of 0.01% to 5% by weight, most preferably at a concentration of 0.1% to 2% by weight. Yet, for instance, a MOC composition according to the invention can be used in a pet-litter product at a concentration of 0.001% to 1% by weight, preferably at a concentration of 0.005% to 0.5% by weight, most preferably at a concentration of 0.01% to 0.3% by weight.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

MOC Activity of the Compounds of Formula (I) as Such

The Compound 1, as defined above, was tested, using current sensory analysis methods, for its ability to reduce the perception of bathroom, tobacco, kitchen, pet and body malodors.

A) To this End, First Various Malodor Model were Prepared, by Admixing Various Ingredients as Per the Below Tables, or According to the Protocol Described:

| Bathroom Malodor | |
| --- | --- |
| Ingredient | % w/w |
| Dipropylene glycol | 62.82 |
| Skatole | 0.91 |
| 2-Naphthalenethiol | 0.91 |
| Thioglycolic acid | 21.18 |
| n-Caproic acid | 6.00 |
| 4-Methylphenyl 3-Methylbutanoate | 2.18 |
| n-Methylmorpholine | 6.00 |
| Total | 100.00 |

| Kitchen Malodor | |
| --- | --- |
| Ingredient | % w/w |
| Diacetyl | 3.85 |
| Pyridine | 3.85 |
| Allyl sulfide | 9.23 |
| Methyl sulfide | 40.00 |
| Heptaldehyde | 3.85 |
| Paraldehyde | 1.90 |
| Propionic acid | 36.92 |
| Acetic acid, glacial | 0.40 |
| Total | 100.00 |

| Body Malodor | |
| --- | --- |
| Ingredient | % w/w |
| n-Caproic acid | 30.00 |
| Isovaleraladehyde | 30.00 |
| Phenylacetic acid | 3.00 |
| Butyric acid | 0.25 |

-continued

Body Malodor

| Ingredient | % w/w |
|---|---|
| Indole | 1.50 |
| p-Cresyl isovalerate | 1.50 |
| p-Cresyl phenyl acetate | 2.75 |
| Thioglycolic acid | 5.00 |
| Dipropylene glycol | 26.00 |
| Total | 100.00 |

Pet Malodor

| Ingredient | % w/w |
|---|---|
| Skatole | 0.91 |
| Isovaleric acid | 2.18 |
| Methyl mercaptan (10% w/w in triethylcitrate) | 0.12 |
| Indole (0.5% w/w in Dipropylene glycol) | 1.50 |
| Urea | 1.00 |
| n-Caproic acid | 2.18 |
| Dipropylene glycol | 92.11 |
| Total | 100.00 |

Tobacco Malodor

The tobacco malodor was prepared by extraction of cigarette debris, comprising: ash; filter; and, paper. The debris from 30 smoked Marlboro Red cigarettes (origin: Philip Morris International) was collected in a 500 ml glass powder jar with a screw closure. 300 ml of ethanol was added. The combination was mixed in a Turbula mixer for 8 hours and then filtered through a Whatman Grade 4 filter paper. The filtrate was used as the tobacco malodor.

B) Sample Preparation

In the following description, the test concentration of the malodor sample used in each case was selected so as to provide a perceived malodor intensity, when evaluated in Sniffin' Sticks odor pens as described below, that was approximately of the order of 6 units on the scale described under Section C below.

The malodor concentrations that were perceived as comprising a malodor intensity rating of approximately 6 when evaluated in Sniffin' Sticks odor pens were as follows:
Bathroom malodor: 0.3% by weight in propylene glycol
Kitchen malodor: 30% by weight in propylene glycol
Body malodor: 0.5% by weight in propylene glycol
Pet malodor: 0.5% by weight in propylene glycol
Tobacco malodor: 50% by weight in propylene glycol The test concentration of the Compound 1 used in each of the malodor reduction tests was selected so as to provide a perceived intensity, when evaluated in Sniffin' Sticks odor pens as described below, that was approximately of the order of 6 units on the scale described under Section C below. The concentration of Compound 1 that was perceived as comprising an odor intensity of about 6 when evaluated in Sniffin' Sticks odor pens was 16% by weight in propylene glycol.

Stock solutions were prepared as follows:
Compound 1 32% by weight: 12.8 g of Compound 1 was mixed with 27.2 g of propylene glycol.
Bathroom malodor 0.6% by weight: 0.6 g of bathroom malodor was mixed with 99.4 g of propylene glycol.
Kitchen malodor 60% by weight: 12.0 g of kitchen malodor was mixed with 8.0 g of propylene glycol.
Body malodor 1% by weight: 1.0 g of body malodor was mixed with 99.0 g of propylene glycol.
Pet malodor 1% by weight: 1.0 g of pet malodor was mixed with 99.0 g of propylene glycol.
The tobacco malodor was used as is.

Each sensory test comprised 3 samples: a malodor only sample; a test sample comprising a combination of Compound 1 and the test malodor; and, a Compound 1 only sample. The samples for the sensory tests were prepared as follows: Malodor only sample: in a separate beaker 3.0 g of malodor stock solution was mixed with 3.0 g of propylene glycol. Once fully homogenized, 2.0 g of the resulting solution was applied to the absorbent fiber in the body of a Sniffin' Stick odor pen (origin: Burghart Messtechnik GmbH). The odor pen was immediately capped and allowed to equilibrate for 24 hours before use.

Compound 1 only sample: in a separate beaker 3.0 g of Compound 1 stock solution was mixed with 3.0 g of propylene glycol. Once fully homogenized, 2.0 g of the resulting solution was applied to the absorbent fiber in the body of a Sniffin' Stick odor pen (origin: Burghart Messtechnik GmbH). The odor pen was immediately capped and allowed to equilibrate for 24 hours before use.

Test samples: in a separate beaker 3.0 g of Compound 1 stock solution was mixed with 3.0 g of malodor stock solution. Once fully homogenized, 2.0 g of the resulting solution was applied to the absorbent fiber in the body of a Sniffin' Stick odor pen (origin: Burghart Messtechnik GmbH). The odor pen was immediately capped and allowed to equilibrate for 24 hours before use.

C) Sensory Test Procedure

The samples were assessed by a panel of 19 trained panelists. By "trained panelists" we mean here individuals that had previously been screened for olfactive acuity and were experienced in rating the perfume and malodor intensity. Moreover, the panelists were prior acquainted with the malodor sample before carrying out the malodor reduction efficacy test.

Each test comprised a malodor only sample, a Compound 1 only sample, and a test sample that comprised Compound 1 and the malodor. The samples were presented to the panelists in Sniffin' Sticks odor pens, prepared according to the description in Section B above. Each Sniffin' Stick was labeled with a randomly generated 3 digit code. Sample presentation was blind, balanced, randomized and sequential monadic.

After smelling an identified malodor only reference sample first to familiarize themselves with the malodor, the panelists were asked to rate the malodor intensity and the overall odor intensity of each sample using a linear, labeled line scale, where 0=no odor and 10=extremely strong odor.

The data generated from the panel's evaluations was statistically analyzed in each case using variance analysis (ANOVA) with Duncan's post-hoc analysis ($\alpha=0.05$).

D) Sensory Test Results

The following tables list the Average Perceived Malodor Intensity (APMI) and Average Perceived Overall Odor Intensity (APOOI) for each of the sensory tests. N.S.D next to the APMI or APOOI indicates that the rating is not statistically different from the same rating for the malodor only sample. An asterisk (*) next to the APMI or APOOI indicates that the rating is statistically different (at the 95% confidence level). It must be noted that the APOOI is not related to the pleasantness of the overall odor.

| Bathroom malodor | | | |
|---|---|---|---|
| Sample | Odor Pen Content | APMI | APOOI |
| Malodor Only | 0.006 g bathroom malodor and 1.994 g propylene glycol | 5.02 | 5.68 |
| Compound 1 + Malodor | 0.006 g bathroom malodor, 0.320 g Compound 1 and 1.674 g propylene glycol | 1.61 * | 5.99 NSD |
| Compound 1 Only | 0.320 g Compound 1 and 1.680 g propylene glycol | 0.91 * | 5.75 NSD |

The Compound 1 was efficient at reducing the perceived intensity of bathroom malodor. The average perceived malodor intensity of the "Compound 1+Malodor" sample was significantly lower than the "Malodor Only" sample; meanwhile, there was no significant increase in the average perceived overall odor intensity.

| Kitchen malodor | | | |
|---|---|---|---|
| Sample | Odor Pen Content | APMI | APOOI |
| Malodor Only | 0.60 g kitchen malodor and 1.40 g propylene glycol | 6.02 | 6.35 |
| Compound 1 + Malodor | 0.60 g kitchen malodor, 0.32 g Compound 1 and 1.08 g propylene glycol | 2.49 * | 5.51 NSD |
| Compound 1 Only | 0.32 g Compound 1 and 1.68 g propylene glycol | 0.95 * | 5.78 NSD |

The Compound 1 was efficient at reducing the perceived intensity of kitchen malodor. The average perceived malodor intensity of the "Compound 1+Malodor" sample was significantly lower than the "Malodor Only" sample; meanwhile, there was no significant increase in the average perceived overall odor intensity.

| Body Malodor | | | |
|---|---|---|---|
| Sample | Odor Pen Content | APMI | APOOI |
| Malodor Only | 0.01 g body malodor and 1.99 g propylene glycol | 6.37 | 6.55 |
| Compound 1 + Malodor | 0.01 g body malodor, 0.32 g Compound 1 and 1.67 g propylene glycol | 2.78 * | 5.61 NSD |
| Compound 1 Only | 0.32 g Compound 1 and 1.68 g propylene glycol | 0.83 * | 6.39 NSD |

The Compound 1 was efficient at reducing the perceived intensity of body malodor. The average perceived malodor intensity of the "Compound 1+Malodor" sample was significantly lower than the "Malodor Only" sample; meanwhile, there was no significant increase in the average perceived overall odor intensity.

| Pet Malodor | | | |
|---|---|---|---|
| Sample | Odor Pen Content | APMI | APOOI |
| Malodor Only | 0.01 g pet malodor and 1.99 g propylene glycol | 6.33 | 6.59 |
| Compound 1 + Malodor | 0.01 g pet malodor, 0.32 g Compound 1 and 1.67 g propylene glycol | 4.84 * | 6.70 NSD |
| Compound 1 Only | 0.32 g Compound 1 and 1.68 g propylene glycol | 0.93 * | 6.01 NSD |

The Compound 1 was efficient at reducing the perceived intensity of pet malodor. The average perceived malodor intensity of the "Compound 1+Malodor" sample was significantly lower than the "Malodor Only" sample; meanwhile, there was no significant increase in the average perceived overall odor intensity.

| Tobacco Malodor | | | |
|---|---|---|---|
| Sample | Odor Pen Content | APMI | APOOI |
| Malodor Only | 1.00 g tobacco malodor and 1.00 g propylene glycol | 6.06 | 6.25 |
| Compound 1 + Malodor | 1.00 g tobacco malodor, 0.32 g Compound 1 and 0.68 g propylene glycol | 3.35 * | 5.85 NSD |
| Compound 1 Only | 0.32 g Compound 1 and 1.68 g propylene glycol | 1.27 * | 6.07 NSD |

The Compound 1 was efficient at reducing the perceived intensity of tobacco malodor. The average perceived malodor intensity of the "Compound 1+Malodor" sample was significantly lower than the "Malodor Only" sample; meanwhile, there was no significant increase in the average perceived overall odor intensity.

Example 2

MOC Activity of the Compounds of Formula (I) as Such, Via Odor Suppression and Antibacterial Activity Preparation of Bacterial Solutions Bacterial solutions of four bacterial strains were prepared for MIC test as follows. Stock cultures stored at −80° C. were subcultured onto agar plate media, and incubated at 37° C. for 24 h to obtain single colonies. Single colonies of the primary cultures were inoculated into broth media and incubated at 37° C., 160 rpm overnight. Aliquots of overnight cultures were inoculated into 50 ml of fresh broth media, and incubated at 37° C., 160 rpm. When the OD reached the target value for each strain (see Table 1), cells were harvested by centrifugation at 5000 rpm for 10 min, and then resuspended in the same fresh broth media at the same volume before the centrifugation. Aliquots (1.1 ml) of each cell suspension were diluted in 200 ml of the same broth media as the bacterial solutions for the MIC test.

TABLE 1

Media, aliquots of overnight culture, and target OD of broth cultures for the preparation of bacterial solutions

| Strains | Agar plate media | Broth Media | Aliquots of Overnight Culture | Target OD |
|---|---|---|---|---|
| Staphylococcus aureus DSMZ 1104 | TSA | MH | 1 ml | 0.7-0.9 |
| Staphylococcus haemolyticus ATCC 114126 | TSA | MH | 1 ml | 0.5-0.7 |
| Morganella morganii URI62 | TSA | MH | 1 ml | 0.3-0.5 |
| Streptococcus agalactiae URI3 | Schaedler + 5% sheep blood | WC[c] | 1 ml | 0.6-0.8 |

Note:
[a]TSA, Tryptic Soy Agar (BD Cat No. 236950),
[b]MH, Mueller Hinton Broth (BD Cat No. 211443),
[c]WC, Wilkins-Chalgren (OXOID Cat No. CM0643).

Preparation of Test Material Sample Solutions

Sample solutions of casmirone and reference material (N302) were prepared as follows. Stock solutions of 1% and 20% were prepared in ethanol, and then seven serial dilutions of each stock solution were prepared in ethanol to obtain a total of 16 solutions of casmirone or the reference material. Aliquot (10 µl) of each solution was used for MIC test. The tested final concentrations of each material were 29, 44, 66, 99, 148, 222, 333, 500, 590, 900, 1300, 2000, 3000, 4500, 6700, 10000 ppm.

The test material control was trans-hexenal, a known material for MIC tests and control tests (e.g. see Int J Food Microbiol. 2010 Jan. 1; 136(3):304-9.).

MIC Test

MIC test were performed in 96 well plates. Table 2 shows the schematic positions of sample solutions in 96 well plates. Column 1 contained bacterial solution only (the positive growth control), and column 12 contained growth media only (the negative growth control). Aliquots (100 of sample solutions were mixed with 190 µl of bacterial solutions in growth media, at concentrations of $10^5$ to $10^6$ cfu/ml, in wells of the 96 well plates. Three replicates for solution.

The 96 wells plates were incubated at 37° C., 160 rpm overnight. After incubation, wells of 96 well plates were examined. Turbid wells were regarded as an indication of microbial growth.

Minimal inhibition concentration (MIC) was determined as the lowest concentration where no growth was observed. Average MIC value of the three replicates was calculated against each strain (see Table 3).

TABLE 2

| Schematic positions of samples in 96 well plates | | | | | | | | | | | |
|---|---|---|---|---|---|---|---|---|---|---|---|
| A | Positive growth control | | | 590 ppm | 29 ppm | | | 590 ppm | 29 ppm | | | Negative growth control (no contamination) |
| B | | | | 900 ppm | 44 ppm | | | 900 ppm | 44 ppm | | | |
| C | | | | 1300 ppm | 66 ppm | | | 1300 ppm | 66 ppm | | | |
| D | | | | 2000 ppm | 99 ppm | | | 2000 ppm | 99 ppm | | | |
| E | | | | 3000 ppm | 148 ppm | | | 3000 ppm | 148 ppm | | | |
| F | | | | 4500 ppm | 222 ppm | | | 4500 ppm | 222 ppm | | | |
| G | | | | 6700 ppm | 333 ppm | | | 6700 ppm | 333 ppm | | | |
| H | | | | 10000 ppm | 500 ppm | | | 10000 ppm | 500 ppm | | | |
| | 1 | 2 | 3 | 4 | 5 | 6 | 7 | 8 | 9 | 10 | 11 | 12 |
| | | | | Compound 1 | | | | trans-hexenal | | | | |

TABLE 3

MIC concentrations (in ppm) of the Compound 1 vs various strain of bacteria

| Bateria | MIC of Compound 1 |
|---|---|
| S.. aureus Associated with hygiene | 333 (compound 1 is efficiently active in application) |
| S.. haemolyticus Associated with body odor | 345 (compound 1 is efficiently active in application) |
| M. morganii Associated with urine/bathroom | 900 (compound 1 is efficiently active in application) |
| S. agalactiae Associated with urine/bathroom | 3433 (compound 1 is moderately active in application) |

Compound 1 shows to be an effective antimicrobial ingredient in concentrations compatible with consumer products, as so able to participate to a MOC effect.

The invention claimed is:

1. A method of reducing malodor, comprising treating a malodor source with a malodor counteracting composition comprising a compound of formula (I) in an amount sufficient to inhibit the growth of at least one bacteria selected from the group consisting of S. aureus, S. haemolyticus, M. morganii, and S. agalactiae, (I)

wherein one R group is a hydrogen atom and the other is a hydrogen atom or a $C_{1-3}$ alkyl group; and each carbon-carbon double bond of said compound, independently from each other, can be in a configuration Z or E or a mixture thereof.

2. The method of claim 1, wherein both R's are a hydrogen atom.

3. The method of claim 1, wherein the compound of formula (I) is selected from the group consisting of (4E,8E)-4,8-cyclododecadien-1-one, (4Z,8E)-4,8-cyclododecadien-1-one, (4E,8Z)-4,8-cyclododecadien-1-one, (4E,8E)-12-methylcyclododeca-4,8-dienone, (4E,8Z)-12-methylcyclododeca-4,8-dienone, (4Z,8E)-12-methylcyclododeca-4,8-dienone, 2-methylcyclododeca-4,8-dienone and mixtures thereof.

4. The method of claim 1, wherein the compound of formula (I) is:
4,8-cyclododecadien-1-one in the form of a mixture comprising about 99%, w/w of (4E,8E)-4,8-cyclododecadien-1-one and about 1% w/w of the (4Z,8E)-4,8-cyclododecadien-1-one and (4E,8Z)-4,8-cyclododecadien-1-one stereoisomer; or
4,8-cyclododecadien-1-one in the form of a mixture comprising at least 90% w/w of (4E,8Z)A,8-cyclododecadien-1-one and (4Z,8E)-4,8-cyclododecadien-1-one stereoisomers and about 5% w/w of the (4E,8E)-4,8-cyclododecadien-1-one stereoisomer.

5. The method of claim 1, wherein the inhibition of the growth of at least one bacteria selected from the group consisting of *S. aureus, S. haemolyticus, M. morganii*, and *S. agalactiae*, is sufficient to modify, suppress, reduce, decrease or mask the sensory perception of a body, residential or pet malodor.

6. The method of claim 5, wherein the malodor is selected from the group consisting of kitchen, bathroom, tobacco, pet, and body malodor.

7. The method of claim 1, wherein the amount sufficient to inhibit the growth of at least one bacteria selected from the group consisting of *S. aureus, S. haemolyticus, M. morganii*, and *S. agalactiae* is from 300 to 3500 ppm.

\* \* \* \* \*